US012605073B2

(12) United States Patent
Wang

(10) Patent No.: US 12,605,073 B2
(45) Date of Patent: Apr. 21, 2026

(54) VASCULAR STATE MEASUREMENT METHOD AND MEASUREMENT DEVICE THEREOF

(71) Applicant: NATIONAL TSING HUA UNIVERSITY, Hsinchu City (TW)

(72) Inventor: Ting-Wei Wang, Hsinchu City (TW)

(73) Assignee: NATIONAL TSING HUA UNIVERSITY, Hsinchu City (TW)

( * ) Notice: Subject to any disclaimer, the term of this patent is extended or adjusted under 35 U.S.C. 154(b) by 0 days.

(21) Appl. No.: 18/742,287

(22) Filed: Jun. 13, 2024

(65) Prior Publication Data
US 2024/0415393 A1     Dec. 19, 2024

(30) Foreign Application Priority Data

Jun. 14, 2023     (TW) ................................. 112122272

(51) Int. Cl.
    *A61B 5/02*        (2006.01)
    *A61B 5/05*        (2021.01)
(52) U.S. Cl.
    CPC ............ *A61B 5/02007* (2013.01); *A61B 5/05* (2013.01)

(58) Field of Classification Search
None
See application file for complete search history.

(56) References Cited

U.S. PATENT DOCUMENTS

2019/0240486 A1*  8/2019  Simon ................ A61N 1/36025
2024/0197188 A1*  6/2024  Gargiulo ................ A61B 5/282

* cited by examiner

*Primary Examiner* — Yi-Shan Yang
(74) *Attorney, Agent, or Firm* — Birch, Stewart, Kolasch & Birch, LLP

(57)               ABSTRACT

The vascular state measurement method includes: performing a first eddy current induction measurement to a target vessel by a first measurement range to derive a first signal characteristic difference; adjusting at least one of a first terminal position and a second terminal position of the first measurement range to form a second measurement range; performing a second eddy current induction measurement to the target vessel by the second measurement range to derive a second signal characteristic difference; and performing at least one action according to the first signal characteristic difference and the second signal characteristic difference, wherein the at least one action is select from determining an optimal detection section of the target vessel and estimating at least one stenosis or sclerosis location of the target vessel.

18 Claims, 10 Drawing Sheets

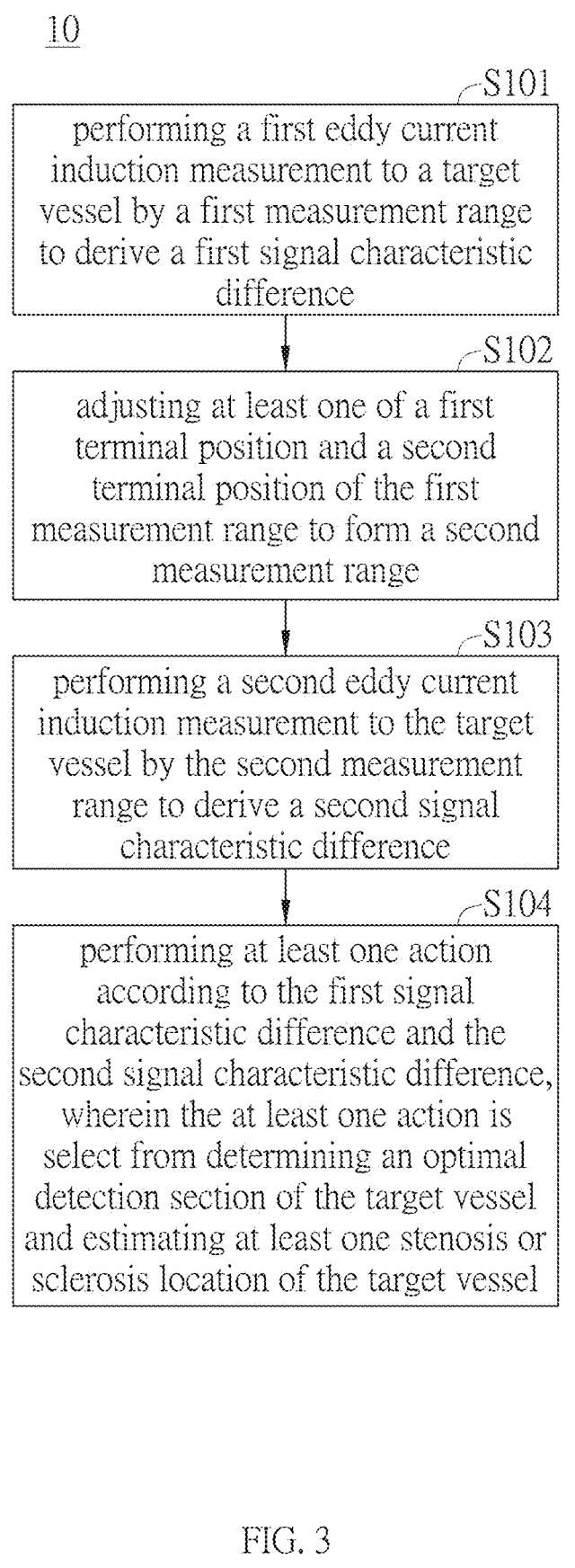

10

S101 performing a first eddy current induction measurement to a target vessel by a first measurement range to derive a first signal characteristic difference

S102 adjusting at least one of a first terminal position and a second terminal position of the first measurement range to form a second measurement range

S103 performing a second eddy current induction measurement to the target vessel by the second measurement range to derive a second signal characteristic difference

S104 performing at least one action according to the first signal characteristic difference and the second signal characteristic difference, wherein the at least one action is select from determining an optimal detection section of the target vessel and estimating at least one stenosis or sclerosis location of the target vessel

FIG. 3

VASCULAR STATE MEASUREMENT METHOD AND MEASUREMENT DEVICE THEREOF

FIELD OF THE INVENTION

The present invention relates to a vascular state measurement method and a vascular state measurement device; in particular, the present invention relates a vascular state measurement method and a vascular state measurement device that which performs the eddy current induction measurement to a target blood vessel by different measurement ranges.

BACKGROUND OF THE INVENTION

With the aging population, changes in modern dietary habits and irregular lifestyles, blood vessel is prone to block by accumulating fat or other impurities into the blood vessel. When the accumulated fat or other impurities can not be eliminated or metabolized, the accumulated fat or other impurities will be accumulated and formed into plaques inside the blood vessel, the plaques cause the blood vessel narrow and affect the blood supply function of the blood vessel. The situation is known as vascular stenosis. On the other hand, people are prone to overweight and have bad habits such as smoking or an oily, greasy and/or salt diet, which leads the blood vessel to loss elasticity. The situation is known known as arteriosclerosis. the vascular stenosis or arteriosclerosis causes systemic decline and becomes the root cause of various fatal diseases. Especially, the carotid artery stenosis is the most dangerous condition of vascular stenosis. Specifically, the carotid artery stenosis is also a hidden killer of stroke. In a narrow carotid artery, the local blood flow velocity accelerates and causes turbulence, which increases the probability of thrombosis and can lead to ischemic stroke.

Due to vascular stenosis and arteriosclerosis being chronic vascular diseases, patients may not necessarily experience symptoms or feel the condition worsen in their daily lives. In clinical practice, if the patients feel symptoms appear, the vascular status is likely to be a severe vascular embolism or sclerosis, and the best treatment opportunity is missed. To perform early evaluation and/or diagnosis of vascular stenosis and arteriosclerosis, an ultrasound apparatus is often used in clinical practice to regularly track and monitor vascular stenosis and arteriosclerosis. For example, an ultrasound apparatus with transducer for neck can be used to track the vascular status of the carotid artery. However, the ultrasound apparatus is a large-scale medical apparatus that is not easily popularized in small clinics or daily measurements. Besides, the ultrasound apparatus needs to be operated by professional operator. Therefore, the large-scaled ultrasound apparatus cannot be applicated in real-time monitoring for the vascular status.

Regarding to conventional real-time detections, electromagnetic coils can be used to monitor blood vessels by using electromagnetic effect. However, the electromagnetic coils are not easy to position the location of vascular embolism or sclerosis, and the electromagnetic coils are also difficult to determine the optimal detection section of the target vessel. Therefore, how to determine/position the vascular embolism or sclerosis and/or determine the optimal detection section of the target vessel will be the technical bottleneck of the technical field.

SUMMARY OF THE INVENTION

One of the objects of the present invention is to provide a method and device for preliminarily positioning the location of vascular embolism or sclerosis and determining a proper/optimal detection section of the target vessel.

The disclosure provides a vascular state measurement method. The vascular state measurement method includes: performing a first eddy current induction measurement to a target vessel by a first measurement range to derive a first signal characteristic difference; adjusting at least one of a first terminal position and a second terminal position of the first measurement range to form a second measurement range; performing a second eddy current induction measurement to the target vessel by the second measurement range to derive a second signal characteristic difference; and performing at least one action according to the first signal characteristic difference and the second signal characteristic difference, wherein the at least one action is select from determining an optimal detection section of the target vessel and estimating at least one stenosis or sclerosis location of the target vessel.

The disclosure provides a vascular state measurement device. The vascular state measurement device includes a coil set and a control module. The coil set has a plurality of coils arranged in order. The control module is coupled to the coil set and configured to: select a first coil and a second coil from the plurality of coils; perform a first eddy current induction measurement, by the first coil and the second coil, to a target vessel to derive a first signal characteristic difference, wherein the first coil corresponds to a first terminal position of a first measurement range and the second coil corresponds to the second terminal position of the first measurement range; replace at least one of the first coil and the second coil, by selecting at least one none selected coil of the plurality of coils, to form a second measurement range; perform a second eddy current induction measurement to the target vessel by the second measurement range to derive a second signal characteristic difference; and perform at least one action according to the first signal characteristic difference and the second signal characteristic difference, wherein the at least one action is select from determining an optimal detection section of the target vessel and estimating at least one stenosis or sclerosis location of the target vessel.

The vascular state measurement method and the vascular state measurement device of the present invention performs two eddy current induction measurements to two detection locations of the target vessel. By comparing the differences between the signal characteristics derived by the two eddy current induction measurements, the stenosis or sclerosis location of the target vessel can be positioned or an optimal detection section of the target vessel can be estimated based on the first signal characteristic difference and the second signal characteristic difference. On the other hands, the vascular state measurement device of the present invention can be made by conventional circuit process, therefore, the cost and size can be reduced. Accordingly, the vascular state measurement device is able to be used for real-time, portable and/or wearable detection.

BRIEF DESCRIPTION OF THE DRAWINGS

The accompanying drawings are presented to aid in the description of various aspects of the disclosure and are provided solely for illustration of the aspects. To simplify the drawings and highlight the contents to be presented in the drawings, the well-known structures or elements in the drawings may be drawn in a simple schematic manner or presented in an omitted manner. For example, the number of elements may be singular or plural. These drawings are provided only to explain these aspects and not to limit thereof.

FIG. 3 is a flowchart of a blood vascular state measurement method according to an embodiment of the present invention.

DETAILED DESCRIPTION OF THE PREFERRED EMBODIMENTS

Even though the terms such as "first", "second", and "third" may be used to describe an element, a part, a region, a layer, and/or a portion in the present specification, these elements, parts, regions, layers and/or portions are not limited by such terms. Such terms are used to differentiate an element, a part, a region, a layer, and/or a portion from another element, part, region, layer, and/or portion. Therefore, in the following discussions, a first element, portion, region, or portion may be called a second element, portion, region, layer, or portion, and do not depart from the teaching of the present disclosure. The terms "comprise," "include", or "have" used in the present specification are open-ended terms and mean to "include", but not limited to As used herein, the term "coupled to" in the various tenses of the verb "couple" may mean that element A is directly connected to element B or that other elements may be connected between elements A and B (i.e., that element A is indirectly connected with element B).

The terms "approximate" or "essentially" used in the present specification include the value itself and the average values within the acceptable range of deviation of the specific values confirmed by a person having ordinary skill in the current art, considering the specific measurement discussed and the number of errors related to such measurement (that is, the limitation of the measurement system). For example, "about" may mean within one or more standard deviations of the value itself or +30%, +20%, +10%, +5%. In addition, "about", "approximate", or "essentially" used in the present specification may select a more acceptable range of deviation or standard deviation based on optical property, etching property, or other properties. One cannot apply one standard deviation to all properties.

Figure 1:
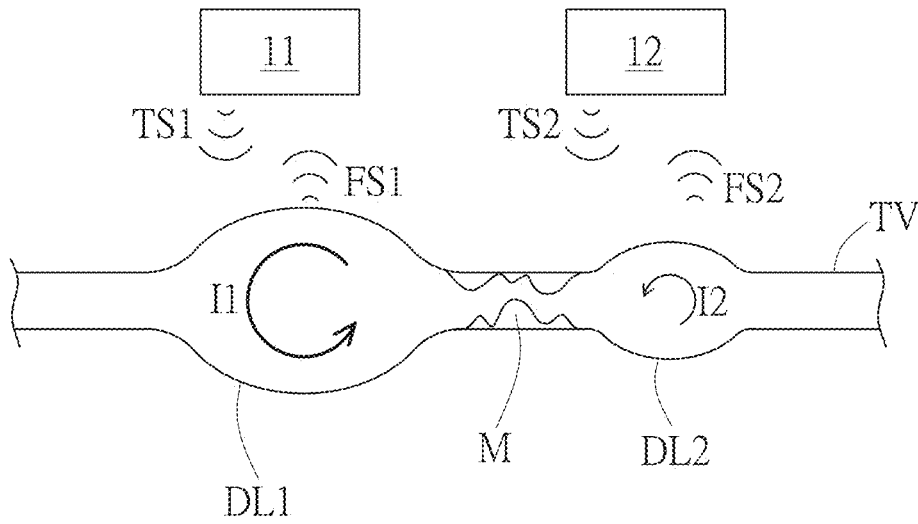
FIG. 1 is a schematic diagram of the eddy current induction according to an embodiment of the present invention.
Figure 2:
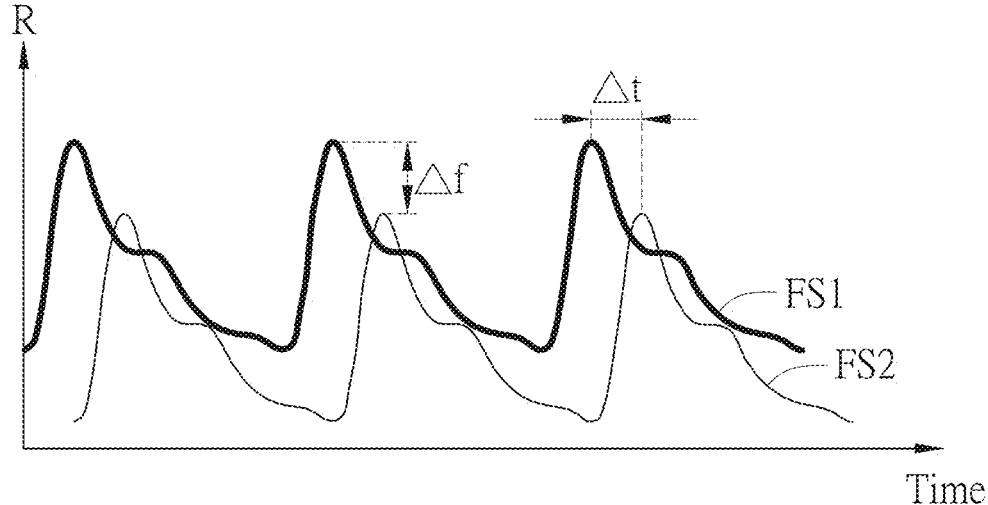
FIG. 2 is a schematic diagram of the measurement results of the eddy current induction according to an embodiment of the present invention.

The Eddy Current Induction Measurement:

Regarding FIGS. 1 and 2, FIG. 1 illustrates a schematic diagram of the eddy current induction measurement according to the present invention. As shown in FIG. 1, electromagnetic waves emitting components 11, 12 are configured to transmit, respectively, a first transmitted electromagnetic signal (TS1) to a first detection location (DL1) of the target vessel (TV) and a second transmitted electromagnetic signal (TS2) to a second detection location (DL2) of the target vessel (TV). More specifically, the electromagnetic waves emitting components 11, 12 may be coupled with a high-frequency signal provider such as signal generator, resonant circuit or radio circuit. The high-frequency signal provider provides the electromagnetic waves emitting components 11, 12 a high-frequency electrical signal. Each of the electromagnetic waves emitting components 11, 12 converts the high-frequency electrical signal to the first transmitted electromagnetic signal (TS1) or the second transmitted electromagnetic signal (TS2), respectively. In an embodiment, the frequency of the first transmitted electromagnetic signal (TS1) and the second transmitted electromagnetic signal (TS2) can be set in a range from 1 MHz to 10 MHz. Accordingly, the range arrangement provides better penetration depth and resolution to blood vessels under the skin. However, the present invention does not limit the frequency of the first transmitted electromagnetic signal (TS1) and the second transmitted electromagnetic signal (TS2). The frequency of the first transmitted electromagnetic signal (TS1) and the second transmitted electromagnetic signal (TS2) can be configured according to the desired depth or resolution of target vessels.

The first detection location (DL1) and the second detection location (DL2) of the target vessel (TV) can be treated as a planar conductor. Therefore, each of the first detection location (DL1) and the second detection location (DL2) of the target vessel (TV) is respectively induced by the first transmitted electromagnetic signal (TS1) and the second transmitted electromagnetic signal (TS2) to generate eddy currents (I1) and (I2), respectively. The eddy currents (I1) and (I2) formed at the first detection location (DL1) and the second detection location (DL2) of the target vessel (TV) are varied depending on the vascular status of the first detection location (DL1) and the second detection location (DL2), such as the magnitude, frequency, and/or peak time of the eddy currents (I1) and (I2). For example, if an accumulated material (M) is located between the first detection location (DL1) and the second detection location (DL2) of the target vessel (TV). The accumulated material (M) causes embolism, and the pressure of the blood flow at the first detection location (DL1) is different from the second detection location (DL2). the pressure difference results in different level of contraction/relaxation at the first detection location (DL1) and the second detection location (DL2) of the target vessel (TV), which affects the generation of the eddy currents (I1) and (I2). The example shown in FIG. 1 is only intended to illustrate that the accumulated material (M) will cause the difference in the level of contraction/relaxation between the first detection location (DL1) and the second detection location (DL2), the different level of contraction/relaxation and/or the generation of the eddy currents (I1) and (I2) is not limited by the example shown in FIG. 1. In another example, the pulse wave velocity (PWV) within the target vessel (TV) will affect the peak time difference in the generation of eddy currents (I1) and (I2). Specifically, the contraction/relaxation time difference caused by a blood pulse propagation between the first detection location (DL1) and the second detection location (DL2) of the target vessel (TV) will result in a time difference for the generation of eddy currents (I1) and (I2). In addition, the PWV is affected by the hardening level of the target vessel (TV).

The eddy currents (I1) and (I2) generated at the first detection location (DL1) and the second detection location (DL2) will generate corresponding a first feedback electromagnetic signal (FS1) and a second feedback electromagnetic signal (FS2). The signal characteristics difference (such as frequency, peak time difference) between the first feedback electromagnetic signal (FS1) and the second feedback electromagnetic signal (FS2) will be varied according to eddy currents (I1) and (I2). More specifically, radiation receiving components (such as the radiation emission components 11 and 12) are configured to receive the first feedback electromagnetic signal (FS1) and the second feedback electromagnetic signal (FS2). The received first feedback electromagnetic signal (FS1) and the received second feedback electromagnetic signal (FS2) are converted into electrical signals through any conventional electromagnetic signal processing means. It should be noted that the first feedback electromagnetic signal (FS1) and the second feedback electromagnetic signal (FS2) are not limited to be received by the radiation emission components 11 and 12 that emit the first transmitted electromagnetic signal (TS1) and the second transmitted electromagnetic signal TS2. In other words, the radiation receiving components can be set adjacent to the radiation emission components 11 and 12 to receive the first feedback electromagnetic signal (FS1) and the second feedback electromagnetic signal (FS2).

In order to analysis the signal characteristics differences between the received first feedback electromagnetic signal (FS1) and the received second feedback electromagnetic signal (FS2), any conventional signal process means can be used. For example, the received first feedback electromagnetic signal (FS1) and the received second feedback electromagnetic signal (FS2) can be analyzed through computing element(s) with computing power coupled to radiation emitting components 11, 12 or the radiation receiving components. the computing element(s) performs signal analysis for analyzing the time, frequency, and/or amplitude of a signal, such as spectrum analysis, main frequency analysis, amplitude analysis, or peak time analysis. It should be noted that the received first feedback electromagnetic signal (FS1) and the received second feedback electromagnetic signal (FS2) are not necessary to convert into electrical signals. For example, the signal type of the received first feedback electromagnetic signal (FS1) and the received second feedback electromagnetic signal (FS2) is based on the computing element. Once the computing element or signal analysis means is able to analyze electromagnetic signals, the first feedback electromagnetic signal (FS1) and the second feedback electromagnetic signal (FS2) are not necessary to convert into electrical signals.

The example signal characteristic difference is shown in FIG. 2. The X-axis represents time or time-dependent data (such as the Nth data), and the Y-axis represents the response (R). The response (R) is a measurable numerical result caused by the first feedback electromagnetic signal (FS1) and the second feedback electromagnetic signal (FS2), and the response (R) can be amplitude, frequency, frequency change, inductance value, inductance change, or other signal parameters. The signal characteristic difference, such as a frequency difference ($\Delta$f) between the first feedback electromagnetic signal (FS1) and the second feedback electromagnetic signal (FS2) due to the differences of the generation of the eddy currents (I1) and (I2), the peak time difference ($\Delta$T) between the first feedback electromagnetic signal (FS1) and the second feedback electromagnetic signal (FS2), and/or other parameters.

The Vascular State Measurement Method 10:

The vascular state measurement method includes: performing a first eddy current induction measurement to a target vessel by a first measurement range to derive a first signal characteristic difference (S101); adjusting at least one of a first terminal position and a second terminal position of the first measurement range to form a second measurement range (S102); performing a second eddy current induction measurement to the target vessel by the second measurement range to derive a second signal characteristic difference (S103); and performing at least one action according to the first signal characteristic difference and the second signal characteristic difference, wherein the at least one action is select from determining an optimal detection section of the target vessel and estimating at least one stenosis or sclerosis location of the target vessel (S104).

Figure 4A:
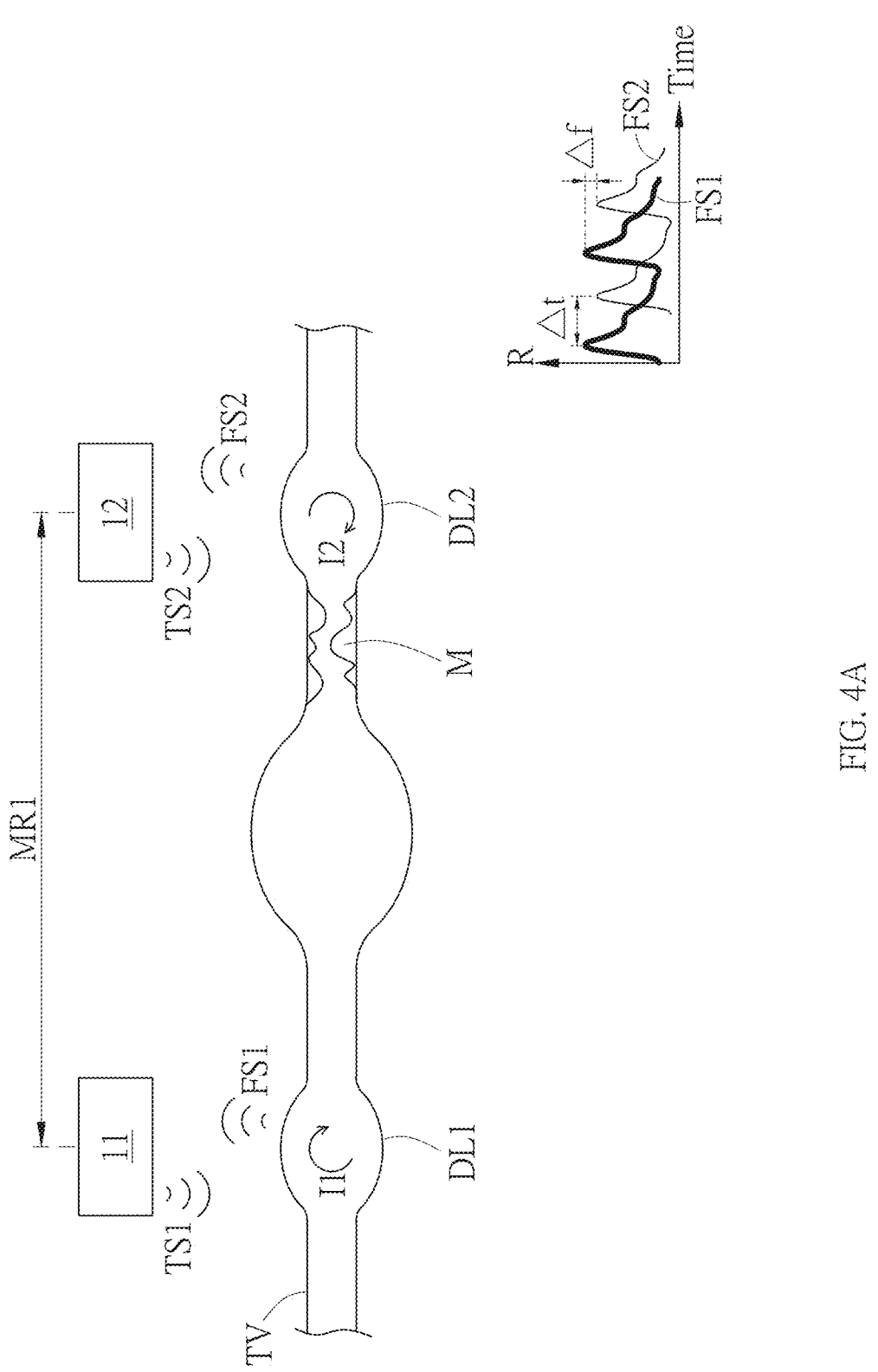
FIGS. 4A to 4C are schematic diagrams of a blood vascular state measurement method according to an embodiment of the present invention.
Figure 4B:
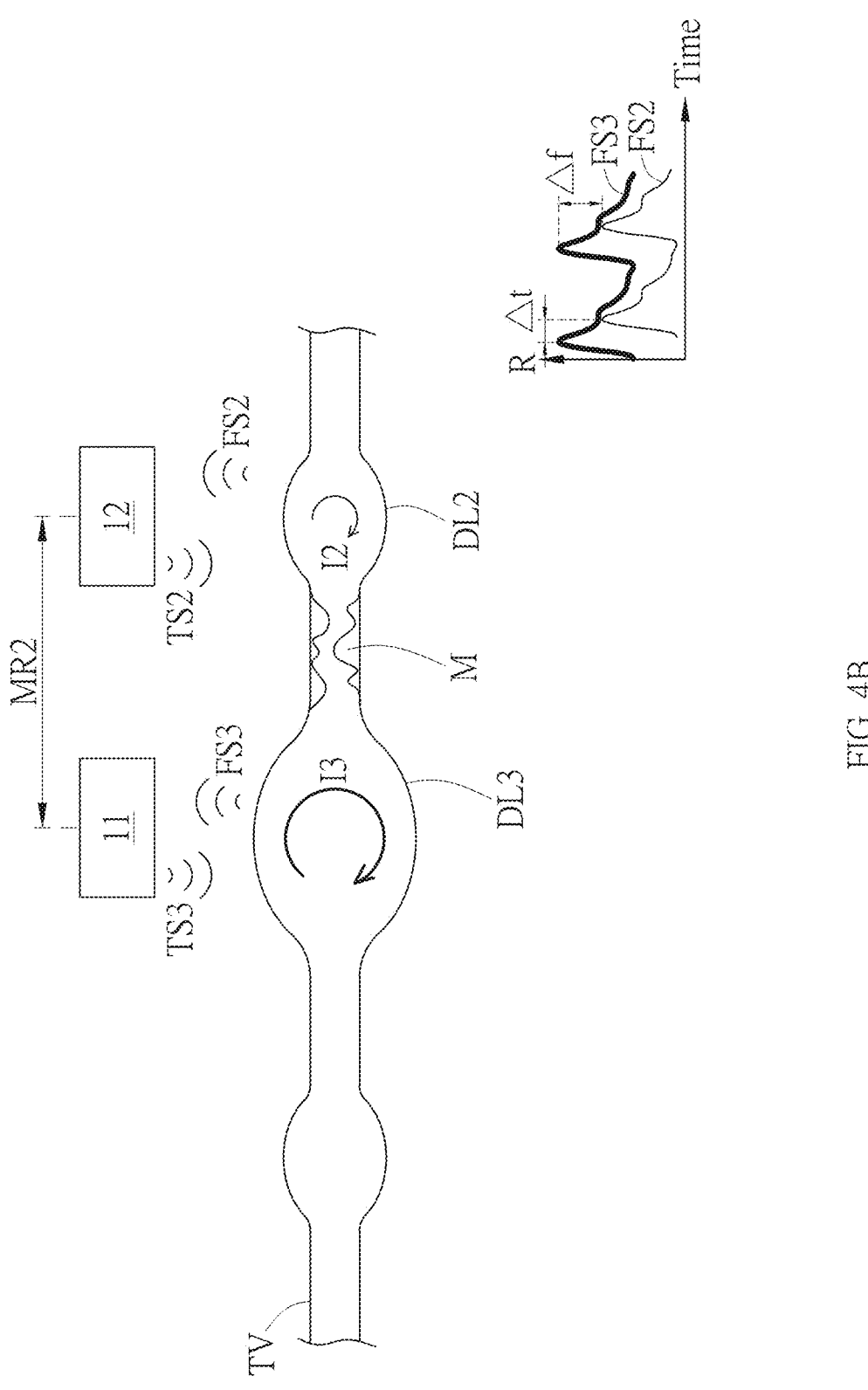
Figure 4C:
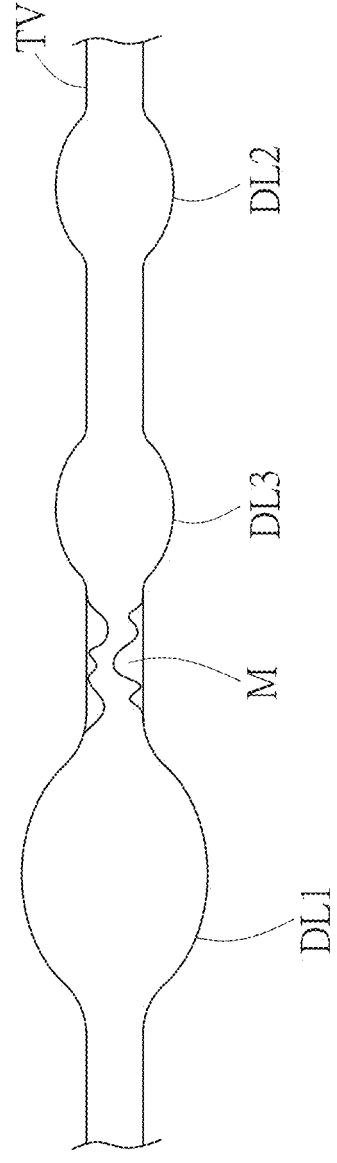

Referring to FIGS. 4A to 4C, FIGS. 4A to 4C illustrate the process for adjusting the first measurement range (MR1) to the second measurement range (MR2) to position/determine an optimal detection section of the target vessel (TV) or the possible location of vascular stenosis or sclerosis in the target vessel (TV). In step S101, a first measurement is shown in FIG. 4A. During the first measurement, an eddy current induction measurement of the present invention is performed to the target vessel (TV) by the first measurement range (MR1). The first measurement range (MR1) is defined from a first terminal position corresponding to the first detection location (DL1) of the target vessel (TV) to a second terminal position corresponding to the second first detection location (DL2) of the target vessel (TV). After the first measurement, a first signal characteristic difference of the first measurement range (MR1) is derived. In step S102, a second measurement is shown in FIG. 4B. a second measurement range (MR2) is modified from the first measurement range (MR1) by adjusting, for example, the first terminal position of the first measurement range (MR1) to an adjusted terminal position corresponding to a third detection location (DL3) of the target vessel (TV). The third detection location (DL3) is located between the first detection location (DL1) and the detection location (DL2). Therefore, the second measurement range (MR2) will be smaller/narrower than the first measurement range (MR1). After the second measurement, a second signal characteristic difference of the second measurement range (MR2) is derived. By comparing the first signal characteristic difference and the second signal characteristic difference (such as frequency difference $\Delta$f), the stenosis or sclerosis location (M) of the target vessel (TV) can be find or positioned. For example, when the stenosis or sclerosis location (M) of the target vessel (TV) is located between the second detection location (DL2) and the third detection location (DL3), and is closer to the third detection location (DL3) compared to the first detection location (DL1), the second signal characteristic difference obtained from the second measurement will be greater than the first signal characteristic difference obtained from the first measurement. On the contrary, as shown in FIG. 4C, when the stenosis or sclerosis location (M) of the target vessel (TV) is located between the first detection location (DL1) and the third detection location (DL3), in other words, the stenosis or sclerosis location (M) of the target vessel (TV) is within the first measurement range (MR1) but not within the second measurement range (MR2), the second signal characteristic difference obtained from the second measurement will not have significant difference due to the flow resistance of the blood flow between the second detection location (DL2) and the third detection location (DL3) is not influenced by the stenosis or sclerosis location (M). By performing the vascular state measurement method 10, the stenosis or sclerosis location (M) of the target vessel (TV) is detected. It should be noted that the vascular state measurement method 10 of the present invention does not limit the times of measurements. Eddy current induction measurements can be performed to the target vessel (TV) by different measurement ranges at least twice or more. Specifically, with several times of measurements, the signal characteristic differences obtained from the several times of measurements will provide more accurate location for the stenosis or sclerosis location (M). Accordingly, the stenosis or sclerosis location (M) of the target vessel (TV) can be positioned. Therefore, the optimal detection section of the target vessel (TV) can be defined as a section of the target vessel (TV) having an optimal signal response. The optimal signal response can be derived by at least two measurements without extra operations; therefore, a user will easily find the optimal detection section of the target vessel (TV) to regularly detecting or monitoring at least one vascular status of the target vessel (TV), e.g. the status of the stenosis or sclerosis location (M) of the target vessel (TV). On the other hand, the optimal detection section of the target vessel (TV) can be defined as a section of the target vessel (TV), which can be a largest detectable section, a shortest detectable section or a section with largest response of the target vessel (TV), but not limited to. Specifically, the at least two measurement range will provide a scan information of the target vessel (TV) without extra operations; therefore, a user will easily find the section of the target vessel (TV) to be measured without overtraining.

Figures 5A, 5B, 5C:
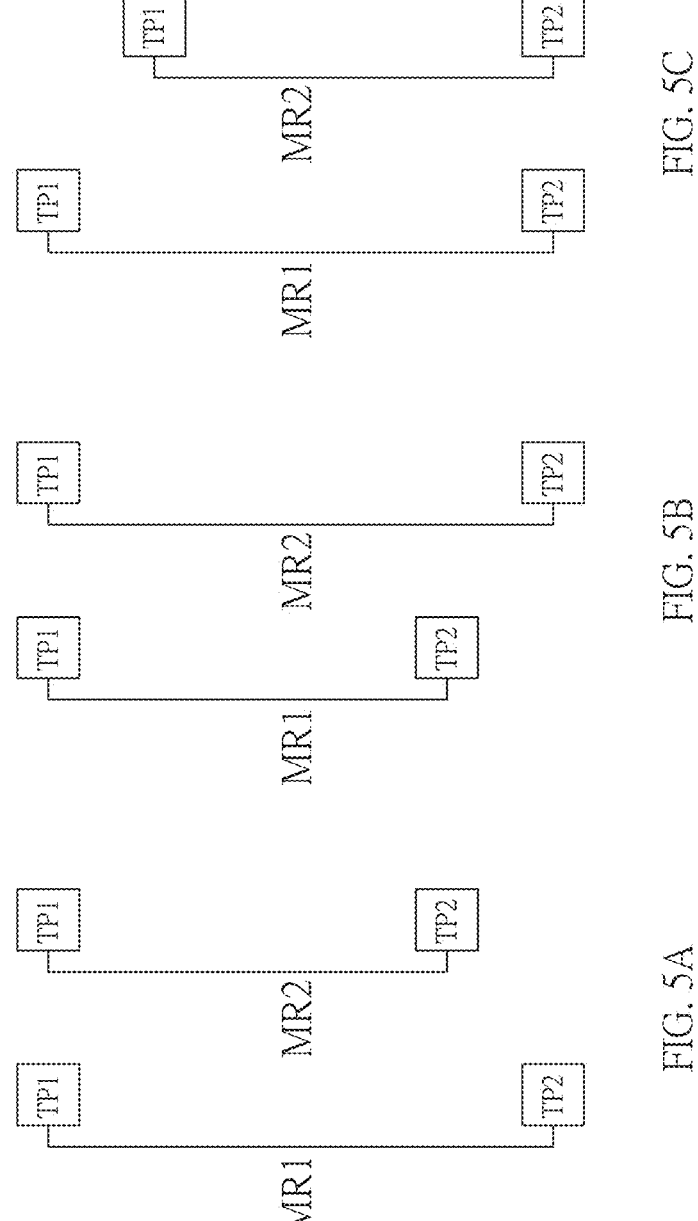
FIGS. 5A to 5G are schematic diagrams of adjusting the measurement range of the vascular state measurement method according to an embodiment of the present invention.
Figures 5D, 5E, 5F, 5G:
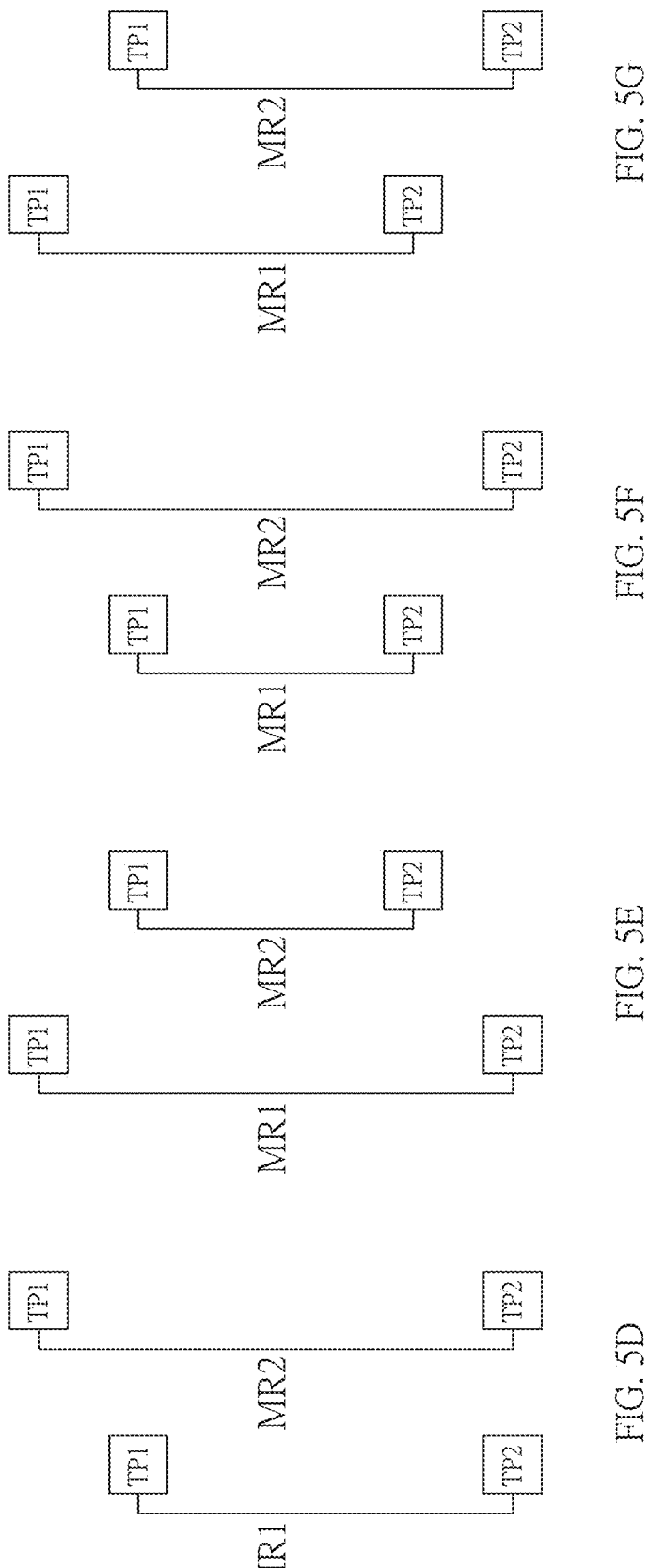

Although in the examples of FIGS. 4A to 4C is performed by fixing the second terminal position corresponding to the second detection location (DL2) and only changing the first terminal position corresponding to the first detection location (DL1), the present invention is not limited to the adjustment method of the measurement range. For example, referring to FIGS. 5A to 5G. In each measurement, one of the first terminal position and the second terminal position (i.e. the starting position and the ending position of the measurement range) can be adjusted. The first measurement range (MR1) may be configured to be greater than, less than, or equal to the second measurement range (MR2). For example, the first terminal position (TP1) of the first measurement range (MR1) is fixed, and the second terminal position (TP2) of the first measurement range (MR1) is adjusted to close (as shown in FIG. 5A) or far away (as shown in FIG. 5B) to/from the first terminal position (TP1) to form the second measurement range (MR2). Or, the second terminal position (TP2) is fixed, the first terminal position (TP1) is adjusted to close (as shown in FIG. 5C) or far away (as shown in FIG. 5D) to/from the second terminal position (TP2) to form the second measurement range (MR2). In addition, the second measurement range (MR2) can be formed by adjusting both of the first terminal position (TP1) and the second terminal position (TP2) of the first measurement range (MR1) to form a narrow (as shown in FIG. 5E) or a wider (as shown in FIG. 5F) the second measurement range (MR2). Or, the distance between the first terminal position (TP1) and the second terminal position (TP2) is fixed and the second measurement range (MR2) is formed by shifting the first measurement range (MR1) (as shown in FIG. 5G).

By using the vascular state measurement method 10, the target vessel (TV) can be scanned to find the optimal detection section of the target vessel (TV). In an embodiment, a further monitoring can be performed to the optimal detection section of the target vessel (TV). Specifically, the further monitoring is performing at least one Eddy current induction measurement of the present invention to the optimal detection section of the target vessel (TV), and deriving the vascular status information of the target vessel (TV) with optimal response from the optimal detection section. The vascular status, such as vascular embolism, vascular sclerosis, pulse transmission velocity, and/or evaluation of blood flow velocity within the optimal detection section of the target vessel (TV). In an embodiment, the vascular status of the target vessel (TV) can be derived by comparing the various parameters measured from different time. For example, comparing the parameters previously measured and currently measured through a long-term and/or multiple measurements to the target vessel (TV). In an embodiment, the vascular state measurement method 10 can be accessed by portable or wearable means. For example, the radiation emission components and/or the radiation receiving components is fabricated on a flexible substrate to be arranged on a subject's skin, but not limited to. Accordingly, the vascular state measurement method 10 can be applied for long-term monitoring without affect the mobility of the subject. The vascular state of the target vessel (TV) can be continuously monitored by the portable or wearable means. The vascular state measurement method 10 provides the optimal detection section of the target vessel (TV); therefore, the vascular state measurement method 10 will improve the signal-to-noise ratio, and ensure that the measurement/monitoring process will not fail due to improper selection of detection locations by an untrained user.

In an embodiment, the vascular state measurement method 10 of the present invention is preferably implemented for carotid artery. Specifically, the carotid artery is mainly divided into the common carotid artery (CCA) and the external carotid artery (ECA) located in the bifurcation area of the carotid artery, and the internal carotid artery (ICA). According to statistics, most of stenosis and/or lesions are located in the bifurcation area of the carotid artery. However, the stenosis and/or lesions are also possible to locate in the common carotid artery, internal carotid artery, or external carotid artery. Therefore, for an ordinary people, the location of the stenosis and/or lesions of the for carotid artery is difficult to position. The vascular state measurement method 10 of the present invention provides the optimal detection section of the carotid artery or the stenosis or sclerosis location of the carotid artery without complex operations. An ordinary people can effectively and quickly find out the optimal detection section of the carotid artery and prevent poor detection results or fails.

Figure 6:
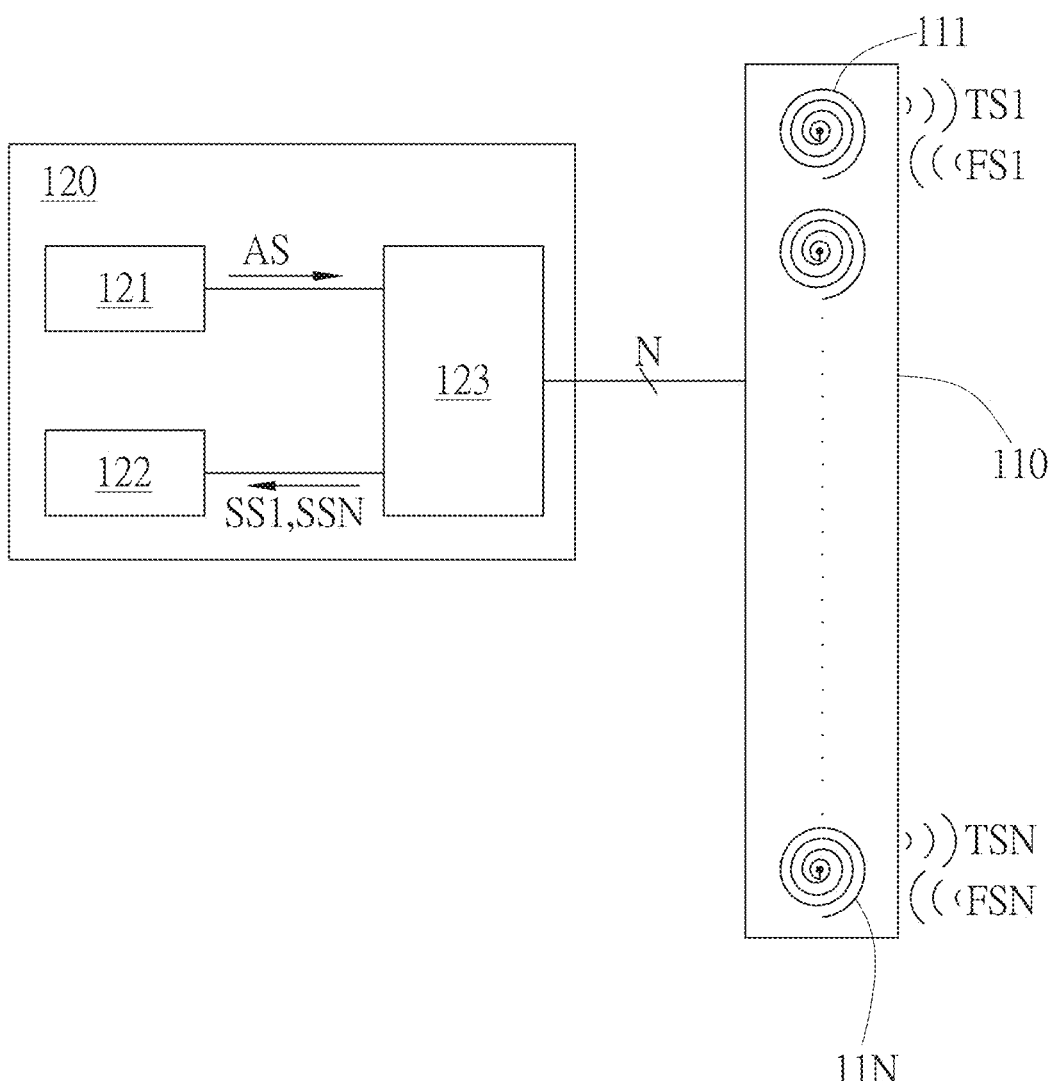
FIG. 6 is a block diagram of a blood vascular state measurement device according to an embodiment of the present invention.

Vascular State Measurement Device 100:

The present invention provides a vascular state measurement device for applying the vascular state measurement method 10. Referring FIG. 6, the vascular state measurement device 100 includes a coil set 110 and a control module 120. The coil set 110 has a plurality of coils 111-11N arranged in order. The control module 120 is coupled to the coil set 110 and configured to: select a first coil 111 and a second coil 11N from the plurality of coils 111-11N; perform a first eddy current induction measurement, by the first coil 111 and the second coil 11N, to a target vessel to derive a first signal characteristic difference, wherein the first coil 111 corresponds to a first terminal position of a first measurement range (MR1) and the second coil corresponds to the second terminal position of the first measurement range (MR1); replace at least one of the first coil 111 and the second coil 11N, by selecting at least one none selected coil 112-11N-1 of the plurality of coils 111-11N, to form a second measurement range (MR2); perform a second eddy current induction measurement to the target vessel by the second measurement range (MR2) to derive a second signal characteristic difference; and perform at least one action according to the first signal characteristic difference and the second signal characteristic difference, wherein the at least one action is select from determining an optimal detection section of the target vessel and estimating at least one stenosis or sclerosis location of the target vessel.

Specifically, the coil set 110 has the plurality of coils 111-11N arranged in order, for example along a direction of extension of the target blood vessel, but not limited to. The plurality of coils 111-11N may be arranged on a skin surface to apply an eddy current induction measurement of the present invention to the target vessel. For example, the target vessel can be positioned by conventional knowledges, e.g. pulse position, or instruments. After confirming the target vessel, the plurality of coils 111-11N are attached to the skin surface over the target vessel. If the target vessel is not straight extension, the plurality of coils 111-11N may be arranged along the extension of the target vessel to have more flexibility in setting. In an embodiment, the plurality of coils 111-11N can be integrated onto a substrate to form the coil set 110. The substrate is, preferably, a flexible substrate to closely attach to the skin surface along the target blood vessel. The integrated coils 111-11N will increase the usability of the coil set 110, for example shorten the setting or removal time. In addition, fabricating the plurality of coils 111-11N on a substrate will ensure that the coils 111-11N have consistent quality, and reduce the manufacturing cost of the coil set 110.

The control module 120 is coupled to the coil set 110. For example, the control module 120 can be an independent control module, such as a computer, tablet, industrial computer, instrument, FPGA, microprocessor, or other programmable or instrument-controlled modules or devices, which may be selected according to the requirement of computing capability. Therefore, if require a high computing power need or a high regulatory/safety need, the control module 120 may be configured by high-level device, such as a computer or instrument. On the other hand, the control module 120 can also be integrated with the coil set 110 as a circuit module on a circuit substrate. For example, the control module 120 is composed by integrated circuits, such as system-on-chip (SOC), application specific integrated circuit (ASIC), and other components. the control module 120 is coupled to the coil set 110 through conductor wires formed on the substrate. The integrated control module 120 and the coil set 110 will reduce the cables or transmission line for communication or signal connection. The integrated control module 120 also prevents affecting the mobility of the subject and reduces discomfort when wearing the vascular state measurement device 100.

In an embodiment. the control module 120 includes a signal generation unit 121, a selection unit 123, and a measurement unit 122. The signal generation unit 121 is configured to provide an AC signal (AS). Specifically, the signal generation unit 121 can be configured to generate an AC signal or convert a DC signal to the AC signal. For example, the signal generation unit 121 is configured to directly generate the AC signal (AS) through composing active components (such as oscillators, timers) and/or passive components (such as resistors, capacitors, inductors). On the other hand, the signal generation unit 121 is configured to convert the DC signal to the AC signal (AS) by resonant circuits or other conventional circuits. By using the resonant circuits to generate the AC signal (AS), it can achieve benefits such as simplifying circuits and saving energy consumption. In an embodiment, the frequency of the AC signal (AS) of the signal generation unit 121 is, preferably, in a range of 1-10 MHz. Accordingly, the range arrangement provides better penetration depth and resolution to blood vessels under the skin.

Figure 7A:
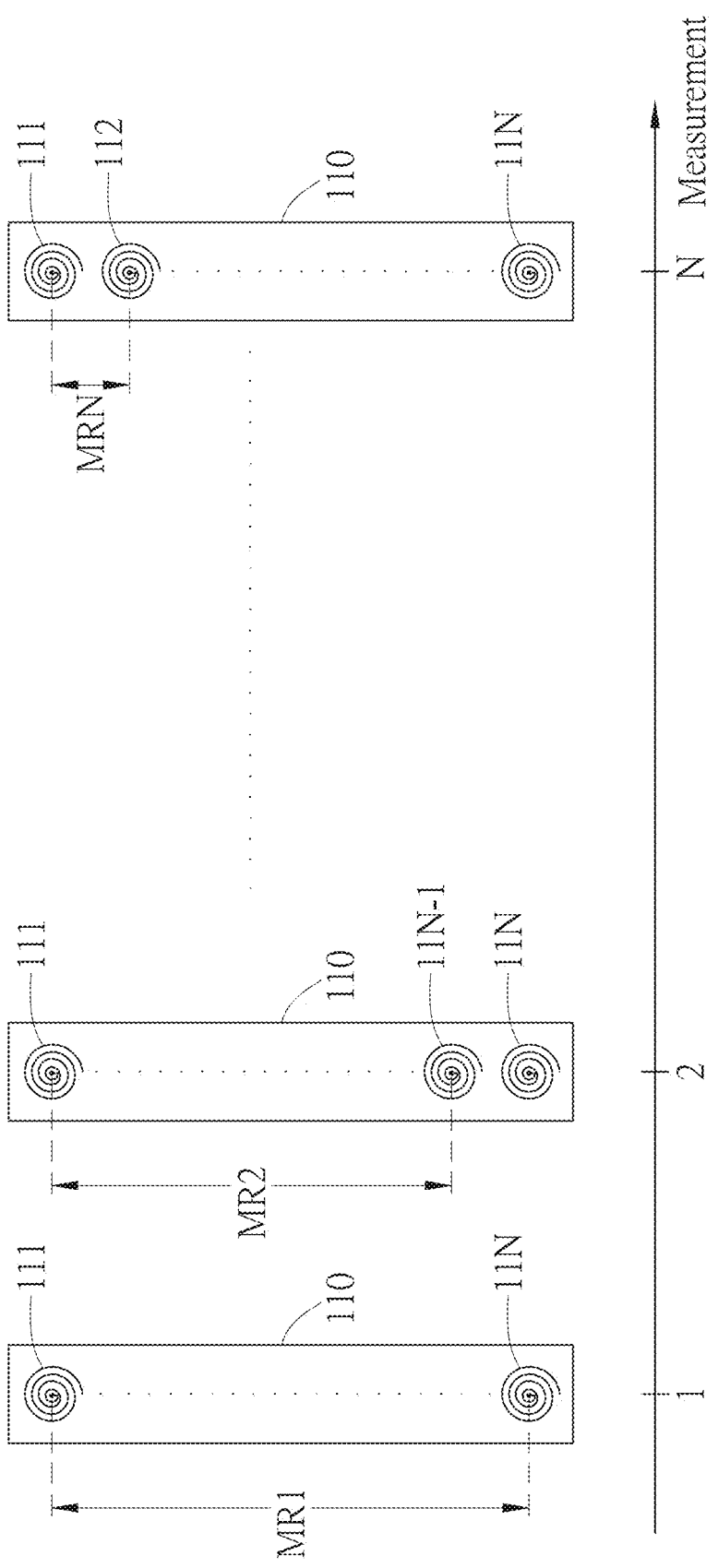
FIGS. 7A and 7B are schematic diagrams of the switching coil of the vascular state measurement device according to an embodiment of the present invention.
Figure 7B:
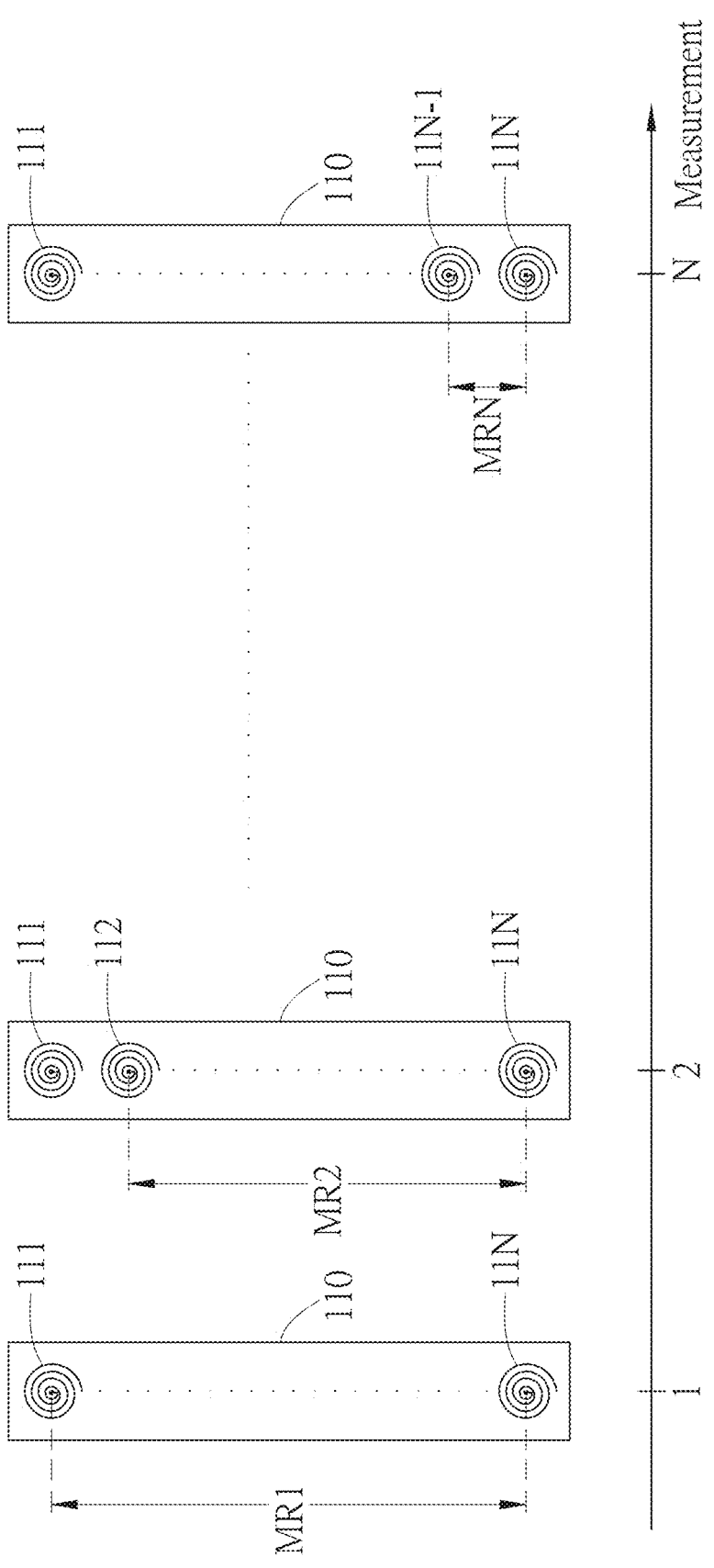

The selection unit 123, for example, is a circuit or component with switching function or selection function, such as multiplexers, selectors, transistor, and switch etc. The selection unit 123 is configured to couple to the coil set 110 and select two of the plurality of coils 111-11N, which are the first coil and the second coil (such as the coil 111 and the coil 11N), to receive the AC signal (AS) provided by the signal generation unit 121. The range between the first coil and the second coil is defined as a first measurement range (MR1). The first coil 111 and the second 11N are configured to emit, respectively, a transmitted electromagnetic signal (TS1) and a transmitted electromagnetic signal (TSN) to the target vessel, and receive a feedback electromagnetic signal (FS1) and a feedback electromagnetic signal (FSN). The feedback electromagnetic signal (FS1) and the feedback electromagnetic signal (FSN) are converted into a sensing signal (SS1) and a sensing signal (SSN) by the first coil 111 and the second 11N. The measurement unit 122 receives the sensing signal (SS1) and the sensing signal (SSN) and calculates the signal characteristics difference for the first measurement range (MR1). Afterwards, the control module 120 controls the selection unit 123 to change at least one of the first coil 111 and second coil 11N to form a second measurement range (MR2). For example, the second coil 11N is replaced by an updated second coil 11N-1. Hence, the second measurement range (MR2) is defined as range between the coil 111 and the coil 11N-1. It should be noted that the present invention is not limited to the selection method of switching the coils 111-11N of the coil set 110 by the selection unit 123. For example, as shown in FIG. 7A, the width of the measurement range can be gradually reduced and approached by changing the second coil through multiple measurements. On the other hand, as shown in FIG. 7B, multiple measurements can be made, each measurement only changing the first coil, gradually narrowing the measurement range and approaching the second coil. However, the above selection methods are only an example, and the coil can also be selected through the configuration method shown in FIG. 5. Therefore, the first measurement range (MR1) and the second measurement range (MR2) do not necessarily need to configured to scan from a large range to a small range, but can also be configured to scan from a small range to a large range or by means of shifting the scanning area with the same scanning size. By scanning, the optimal measurement range and location can be gradually found. On the other hand, the signal difference amplitude between multiple measurements can also be used to identify areas of suspected stenosis or sclerosis in the target vessel.

In an embodiment, a barrier layer is arranged between the coil set 110 and the skin of the subject. The barrier layer has signal permeable portions corresponding to the coils 111-11N of the coil set 110. The signal permeable portions of the barrier layer are configured to allow the electromagnetic signals emitted by the selected coil more directional and less likely to affect each other. The material of the barrier layer is, preferably, a ferrite sheet as a magnetic shielding layer. The barrier layer is used to reduce interference during measurement. Therefore, the barrier layer improves the signal quality and enhancing the signal resolution of the vascular state measurement device 100.

After scanning the target vessel to find the optimal detection location, the vascular status measurement device 100 can perform long-term monitoring after indicating the optimal detection location. For example, performing at least one eddy current induction measurement to the optimal detection location to measure the vascular status information of the target vessel. The vascular status, such as vascular embolism, vascular sclerosis, pulse transmission velocity, and/or evaluation of blood flow velocity within the optimal detection section of the target vessel. In an embodiment, the vascular status of the target vessel (TV) can be derived by comparing the various parameters measured from different time. For example, comparing the parameters previously measured and currently measured through a long-term and/or multiple measurements to the target vessel. In the embodiment, the control module 120 of the vascular status measurement device 100 may also have a communication unit. The communication unit is configured to transmit vascular status information to a host device through a communication link. Specifically, the host device is selected from smartphones, desktops, laptops, and other backend devices. The communication unit is configured to create the communication link with the host device, the communication link can be wireless (such as Bluetooth, wireless network, infrared, etc.) or wired (such as wired network or cable, etc.). Furthermore, programs or APPs can be stored in a memory of the host device. The programs or APPs cause the host device to record or analyze the vascular status information provided by the vascular status measurement device 100. Accordingly, it is possible to achieve long-term tracking of the vascular status of the subjects and evaluate the risk of developing cardiovascular disease or stroke based on the accumulated information on vascular status changes over the long term.

The foregoing disclosure is merely preferred embodiments of the present invention and is not intended to limit the claims of the present invention. Any equivalent technical variation of the description and drawings of the present invention of the present shall be within the scope of the claims of the present invention.

What is claimed is:

1. A vascular state measurement method comprising:
performing a first eddy current induction measurement to a target vessel at a first terminal position and at a second terminal position of the target vessel defining a first measurement range;
deriving a first signal characteristic difference between a first terminal position and a second terminal position based on the first eddy current induction measurement;
adjusting at least one of the first terminal position and the second terminal position of the first measurement range to form a second measurement range;
performing a second eddy current induction measurement to the target vessel at a third terminal position and a fourth terminal position of the target vessel defining the second measurement range;
deriving a second signal characteristic difference between a third terminal position and a fourth terminal position based on the second eddy current induction measurement; and
determining at least one stenosis or sclerosis location within the target vessel according to the first signal characteristic difference and the second signal characteristic difference.

2. The vascular state measurement method of claim 1, wherein the first eddy current induction measurement including:
transmitting a first transmitted electromagnetic signal to the first terminal position of the target vessel, and transmitting a second transmitted electromagnetic signal to the second terminal position of the target vessel; and deriving the first signal characteristic difference according to a first feedback electromagnetic signal from the first terminal position induced by the first transmitted electromagnetic signal and a second feedback electromagnetic signal from the second terminal position induced by the second transmitted electromagnetic signal.

3. The vascular state measurement method of claim 2, wherein the first signal characteristic difference at least includes a frequency difference between the first feedback electromagnetic signal and the second feedback electromagnetic signal.

4. The vascular state measurement method of claim 2, wherein the first signal characteristic difference at least includes a time delay between the first feedback electromagnetic signal and the second feedback electromagnetic signal.

5. The vascular state measurement method of claim 1 wherein a detection section of the target vessel is determined according to a larger one of the first signal characteristic difference and the second signal characteristic difference.

6. The vascular state measurement method of claim 1, further comprising:
performing at least one eddy current induction measurement within a detection section of the target vessel determined by the first signal characteristic difference and the second signal characteristic difference to derive at least one vascular state of the target vessel within the detection section.

7. The vascular state measurement method of claim 1, wherein the second measurement range is smaller than the first measurement range.

8. The vascular state measurement method of claim 1, wherein the second measurement range is formed by adjusting one of the first terminal position and the second terminal position of the first measurement range.

9. The vascular state measurement method of claim 1, when the second signal characteristic difference is greater than the first characteristic difference, a stenosis or sclerosis location of the target vessel is determined to be located within the second measurement range and closer to the terminal position or the terminal position defining the second measurement range as compared with the first measurement range.

10. A vascular state measurement device comprising:
a coil set having a plurality of coils arranged in order; and
a control module coupled to the coil set and configured to:
select a first coil and a second coil from the plurality of coils;
perform a first eddy current induction measurement to a target vessel, by the first coil corresponds to a first terminal position and the second coil corresponds to a second terminal position of the target vessel wherein the first terminal position and the second terminal position define a first measurement range;
derive a first signal characteristic difference between the first terminal position and the second terminal position based on the first eddy current induction measurement;
adjust at least one of the first terminal position and the second terminal position of the first measurement range, by selecting at least one non-selected coil of the plurality of coils, to form a second measurement range;
perform a second eddy current induction measurement to the target vessel at a third terminal position and at a fourth position of the target vessel defining a second measurement range;

derive a second signal characteristic difference between the third terminal position and the fourth terminal position based on the second eddy current induction measurement; and determine at least one stenosis or sclerosis location within the target vessel according to the first signal characteristic difference and the second signal characteristic difference.

11. The vascular state measurement device of claim 10, wherein the control module includes:

a signal generation unit configured to provide an AC signal;

a selection unit coupled to the coil set and configured to select the first coil and the second coil configured to be activated by the AC signal;

wherein the first coil is configured to transmit a first transmitted electromagnetic signal to a first detection location of the target vessel, and receive a first feedback electromagnetic signal from the first detection location inducted by the first transmitted electromagnetic signal;

wherein the second coil is configured to transmit a second transmitted electromagnetic signal to a second detection location of the target vessel, and receive a second feedback electromagnetic signal from the second detection location inducted by the second transmitted electromagnetic signal; and a measurement unit configured to derive the first signal characteristic difference between the first feedback electromagnetic and the second feedback electromagnetic signal.

12. The vascular state measurement device of claim 11, wherein the first signal characteristic difference at least includes a frequency difference between the first feedback electromagnetic signal and the second feedback electromagnetic signal.

13. The vascular state measurement device of claim 11, wherein the first signal characteristic difference at least includes a time delay between the first feedback electromagnetic signal and the second feedback electromagnetic signal.

14. The vascular state measurement device of claim 10, wherein a detection section of the target vessel is determined according to a larger one of the first signal characteristic difference and the second signal characteristic difference.

15. The vascular state measurement device of claim 10, wherein the control module is further configured to perform at least one eddy current induction measurement within a detection section of the target vessel determined by the first signal characteristic difference and the second signal characteristic difference to derive at least one vascular state of the target vessel within the detection section.

16. The vascular state measurement device of claim 10, wherein the second measurement range is smaller than the first measurement range.

17. The vascular state measurement device of claim 10, when the second signal characteristic difference is greater than the first characteristic difference, a stenosis or sclerosis location of the target vessel is determined to be located within the second measurement range and closer to the terminal position or the terminal position defining the second measurement range as compared with the first measurement range.

18. The vascular state measurement device of claim 10, wherein the coil set is arranged on a flexible substrate.

* * * * *